United States Patent [19]

Rose

[11] 4,043,364
[45] Aug. 23, 1977

[54] PLIER SET FOR MAKING TORQUING BENDS IN ORTHODONTIC ARCH WIRES

[75] Inventor: Larry A. Rose, Houston, Tex.

[73] Assignee: E.T.M. Corporation, Monrovia, Calif.

[21] Appl. No.: 744,597

[22] Filed: Nov. 24, 1976

[51] Int. Cl.² .......................... B21F 1/00; B21F 7/00; B21D 11/14; A61C 7/00
[52] U.S. Cl. ...................................... 140/106; 32/66; 72/409; 140/149
[58] Field of Search ................. 32/40 R, 66; 72/299, 72/409, 458, 459; 140/93.6, 106, 119, 149

[56] References Cited

U.S. PATENT DOCUMENTS

| | | | |
|---|---|---|---|
| 1,299,103 | 4/1919 | Angle | 32/66 |
| 1,652,814 | 12/1927 | Cary | 140/93.6 |
| 2,783,669 | 3/1957 | Scarborough | 72/409 X |
| 2,868,239 | 1/1959 | Ellis | 140/93.6 |
| 3,146,804 | 9/1964 | Wallshein | 140/106 |
| 3,244,201 | 4/1966 | Wallshein | 140/106 |
| 3,696,654 | 10/1972 | Bohn | 72/299 |

*Primary Examiner*—E. M. Combs
*Attorney, Agent, or Firm*—Christie, Parker & Hale

[57] ABSTRACT

A wire-bending plier set for permanently twisting a portion of orthodontic arch wire about the wire axis to enable application of a torque force to a malpositioned tooth. The plier is configured to grip the wire at spaced-apart positions between which the twisting bend is to be made. A lever or key is then engaged with the wire between the gripped areas, and the key is rotated about the wire axis to stress the wire beyond the elastic limit and impart the desired twist.

8 Claims, 11 Drawing Figures

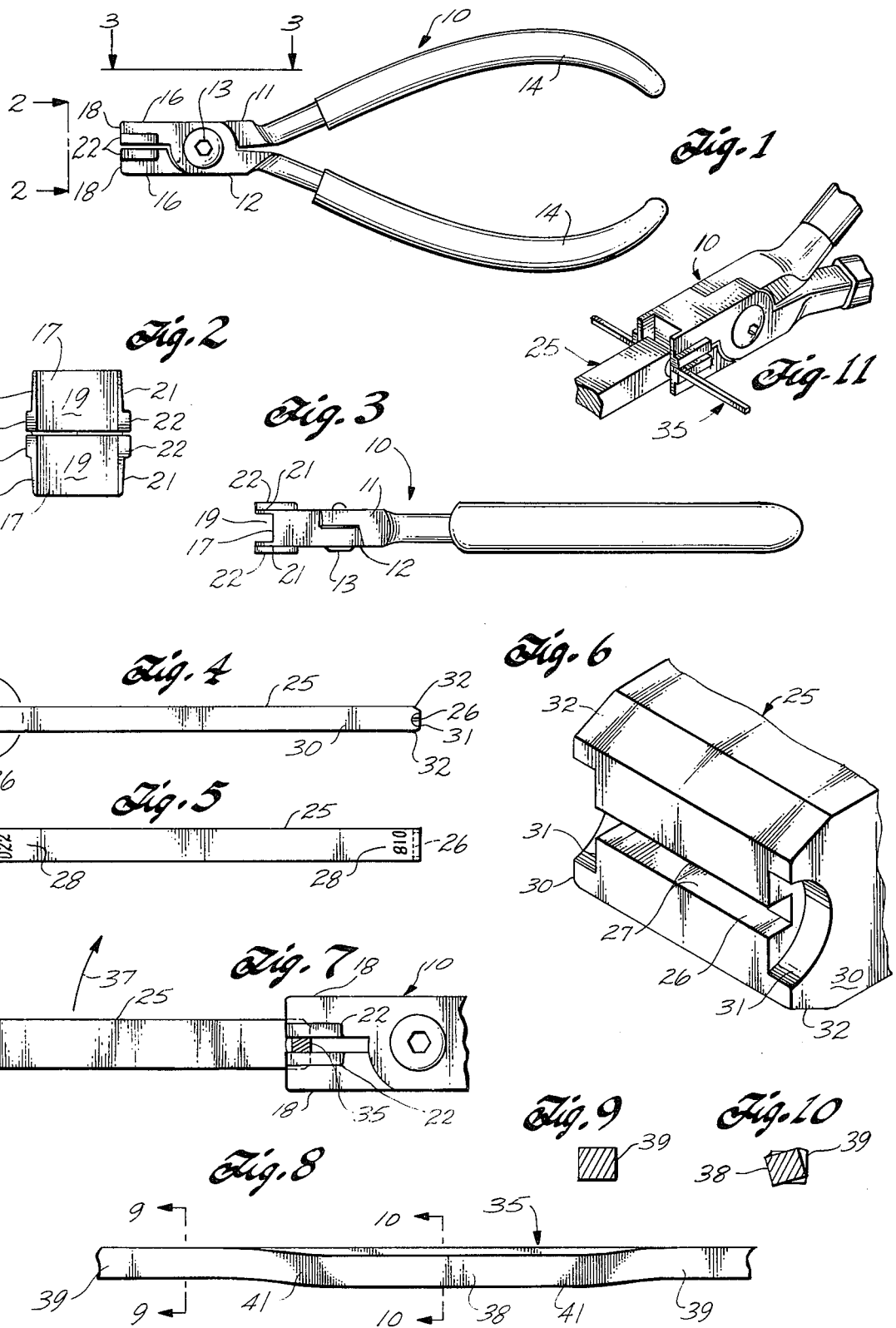

PLIER SET FOR MAKING TORQUING BENDS IN ORTHODONTIC ARCH WIRES

BACKGROUND OF THE INVENTION

A well-known orthodontic technique involves use of rectangular-cross-section arch wires in combination with "edgewise" orthodontic brackets to apply corrective forces to malpositioned teeth. The arch wire fits in mating slots in the brackets which are mounted on the teeth, and bends made in the arch wire before installation distort the resilient wire when installed in the brackets, resulting in restoring forces which urge the teeth toward a corrected position for proper occlusion.

A common problem in orthodontics is the repositioning of a tooth having a root or roots which are generally properly located, but where the body or crown of the tooth is angled labially or buccally (toward the lips or cheeks) or lingually (toward the tongue) out of the ideal dental-arch position. Correction of this kind of problem is important not only for cosmetic reasons, but more importantly to insure proper occlusion and chewing function of the teeth. The force applied in order to correct a forward or rearward tilt of a tooth out of normal alignment is called a torquing force because the force tends to rotate the tooth about a mesiodistal axis through the tooth root.

Edgewise techniques are well suited to the application of torque, but the torquing bends which are formed in the arch wire are awkward and time-consuming to make with conventional pliers, and require considerable manipulative skill if an accurate, reproducable twisting bend is to be achieved. It is particularly difficult to form a twisting bend with conventional pliers without distorting other portions of the arch wire, and such distortion is undesirable in that it may result in the application of tooth-moving forces to teeth which are already correctly positioned. The plier assembly of this invention enables rapid and accurate formation of twisted portions of an arch wire to be used in applying torque to one or more teeth.

SUMMARY OF THE INVENTION

Briefly stated, this invention relates to a wire-bending plier set for use with orthodontic arch wire of non-circular cross section. The plier set includes a plier with a pair of hinged arms having handles and opposed tip portions, the arms being pivotally movable with respect to each other about a hinge axis disposed between the handles and tip portions. Each tip portion includes a pair of gripping jaws which are spaced apart in a direction parallel to the hinge axis. The pairs of jaws are aligned so an arch wire can be gripped simultaneously at two axially spaced positions between the jaw pairs, with a central portion of the wire between the axially spaced positions being supported and exposed between the jaws.

A bending member such as an elongated key or bar has an end defining a slot configured to receive and engage the central portion of the arch wire, whereby rotation of the bar about the wire axis will twist the central portion with respect to the axially spaced positions to form a torquing bend in the arch wire. Preferably, slots of different widths are formed at opposite ends of the bar to accommodate two different sizes of arch wire. Recesses are formed at opposite ends of the bar slots to provide a clearance space within which wire twisting may take place without shearing the wire.

DESCRIPTION OF THE DRAWINGS

FIG. 1 is a side elevation of an orthodontic plier according to the invention;

FIG. 2 is an enlarged end view of the plier jaws on line 2—2 of FIG. 1;

FIG. 3 is a top view of the plier on line 3—3 of FIG. 1;

FIG. 4 is a side view of a wire-bending bar used with the plier;

FIG. 5 is a top view of the wire-bending bar;

FIG. 6 is an enlarged perspective view of one tip of the bar;

FIG. 7 is a side elevation of portions of the plier and bar engaged with an arch wire;

FIG. 8 is an enlarged view of a portion of orthodontic arch wire in which a torquing bend has been placed;

FIG. 9 is a section on line 9—9 of FIG. 8;

FIG. 10 is a section on line 10—10 of FIG. 8; and

FIG. 11 is a perspective view of a portion of the plier jaws gripping an arch wire in preparation for making a torquing bend.

DESCRIPTION OF THE PREFERRED EMBODIMENT

A plier 10 according to the invention is shown in FIGS. 1-3 and 11, and includes a pair of conventional plier arms 11 and 12 which are pivotally connected by a hinge-pin bolt 13. Preferably, handle portions of the arms are covered by plastic sheaths 14 for ease of handling. These features are conventional in dental pliers, and, for brevity, will not be described in detail.

Each of arms 11 and 12 terminate in a tip portion 16 having a flat end wall 17 and a pair of gripping jaws 18 extending forwardly (away from the plier hinge axis) from opposite sides of the end wall. Gripping jaws 18 on each tip portion are spaced apart in a direction parallel to the hinge-pin to define an open channel 19 therebetween.

Preferably, each jaw 18 includes a relatively thin flange 21 which is an integral part of the associated plier arm. A hardened tool-steel insert 22 is gold-brazed along the outer surface of the arm and flange.

The pairs of jaws 18 on each tip portion are in face-to-face alignment when the plier is nearly closed as shown in FIGS. 1 and 2. The facing surfaces of the jaws are flat, and these surfaces are parallel when spaced apart about 0.020 inch which is a typical thickness of orthodontic arch wire used with the plier.

The other component of the plier set of this invention is a bending member which is preferably formed as an elongated key or bar 25 as shown in FIGS. 4-6. Each end of the bar defines a rectangular-cross-section slot 26 extending perpendicular to the longitudinal axis of the bar. Sidewalls 27 (FIG. 6) of slot 26 are spaced apart to receive and snugly engage an orthodontic arch wire of a specific dimension.

For example, sidewalls 27 in one of slots 26 may be spaced apart 0.018 inch (preferably with a tolerance of plus 0.001 inch minus nothing) to receive a rectangular-cross-section arch wire having a thickness of 0.018 inch. The sidewalls of the slot at the other end of bar 25 may be spaced apart 0.022 inch (plus 0.001 inch, minus nothing) to receive a rectangular-cross-section arch wire of 0.022 inch thickness. Preferably, marks 28 (FIG. 5) are stamped adjacent each end of the bar to designate the widths of the slots. Other slot sizes can of course be provided in the bar.

As best seen in FIG. 6, side surfaces 30 of bar 25 define semicircular recesses 31 at the opposite ends of each slot 26. Beveled surfaces 32 are provided at the upper and lower edges of each end of the bar on opposite sides of the slot.

Bar 25 is preferably made of hardened tool steel, and the slots and recesses are formed by milling. In a typical configuration, the total bar width is about 0.250 inch and the length of slot 26 between the bases of recesses 31 is about 0.190 inch. For a bar of this size, gripping jaws 18 on each tip portion 16 of the plier arms are spaced apart about 0.265 inch so the bar end will fit easily between the gripping jaws into channel 19.

In use, a rectangular-cross-section arch wire 35 is gripped between jaws 18 as shown in FIG. 11, with the arch wire being positioned adjacent the distal ends of the jaws and aligned substantially parallel to the plier hinge axis. With the wire securely gripped in this position, the end of bar 25 is slipped into channel 19 to engage the arch wire in slot 26 as shown in FIG. 7. The bar is then rotated about the longitudinal axis of the wire as indicated by arrow 37 in FIG. 7 to twist a central portion 38 of the wire which is freely supported between axially spaced positions 39 of the wire which are rigidly held by the jaws. The central portion of the wire is thus twisted with respect to the gripped portions to impart a torquing bend in the wire.

Recesses 31 at opposite ends of the bar slot provide a clearance space within which a pair of spaced-apart twists 41 (FIG. 8) are imparted to the wire as the bar is rotated. As shown in FIGS. 8–10, central portion 38 of the wire is twisted with respect to axially spaced positions 39, and the axially spaced positions remain in alignment with each other because they are securely gripped by the plier jaws during rotation of the bar. The plier set thus provides an ideal torquing bend because the wire portions remote from central portion 38 remain in the original alignment.

Beveled surfaces 32 at the ends of the torquing key or bar insure that the bar can be freely rotated without contacting end walls 17 of the plier tips. Interference of this type will not occur if the arch wire is properly gripped at the distal ends of the jaws.

A plier set having the dimensions discussed above is satisfactory for most orthodontic applications, but other dimensions may of course be used if shorter or longer twisted portions of an arch wire are desired, or for wires of different cross-sectional thickness. The plier set enables formation of torquing bends in a single operation, and insures that the untwisted portions of the wire remain in their original alignment without distortion. Overstressing or breakage of the wire at the twist points is avoided by forming the twists in the wire portions falling within the clearance spaces provided by recesses 31 at opposite ends of the bar slot.

I claim:

1. A wire-bending plier set for use with orthodontic arch wire of non-circular cross section, comprising:

a plier with a pair of hinged arms having handles and opposed tip portions, the arms being pivotally movable with respect to each other about a hinge axis disposed between the handles and tip portions, each tip portion having a pair of gripping jaws which are spaced apart in a direction parallel to the hinge axis, the pairs of jaws being aligned so the arch wire can be gripped at two axially spaced positions between the jaw pairs with a central portion of the wire between the axially spaced positions being supported and exposed between the jaws; and a bending member having an end portion shaped for removable insertion between the plier jaws and being rotatable about the axis of said wire, said end portion defining a slot configured to receive and engage the central portion of the arch wire whereby rotation of the bending member end portion about the wire axis, when said end portion is positioned between said jaws, will twist the central portion with respect to the axially spaced positions to form a torquing bend in the central portion of the arch wire.

2. The plier set of claim 1 wherein the bending member has side surfaces which are recessed adjacent opposite ends of the slot to form clearance spaces within which twists are formed in the arch wire.

3. The plier set of claim 2 wherein the recesses in the side surfaces are about 0.030 inch deep.

4. The plier set of claim 2 wherein the end portion of the bending member defines beveled surfaces on opposite sides of the slot and extending generally parallel to the slot.

5. The plier set of claim 2 wherein the bending member is an elongated bar having said slot formed in one end portion thereof, and having a second slot formed in the opposite end portion, the two slots being of different widths.

6. The plier set of claim 1 wherein the opposed gripping jaws on the tip portions have facing surfaces which are substantially parallel when the jaws are separated by about 0.020 inch.

7. The plier set of claim 6 wherein the facing surfaces of the gripping jaws are flat.

8. The plier set of claim 7 wherein the bending member is an elongated bar having said slot formed in one end portion thereof, and having a second slot formed in the opposite end portion of the bar, the slots being of different widths to engage arch wires of two different sizes, the bar having side surfaces which are recessed adjacent opposite ends of each slot to form clearance spaces within which twists are formed in the central portion of the arch wire.

* * * * *

UNITED STATES PATENT AND TRADEMARK OFFICE
CERTIFICATE OF CORRECTION

PATENT NO. : 4,043,364
DATED : August 23, 1977
INVENTOR(S) : Larry A. Rose

It is certified that error appears in the above-identified patent and that said Letters Patent are hereby corrected as shown below:

Column 2, line 38, after "hinge-pin" insert -- axis--.

Signed and Sealed this

Third Day of October 1978

[SEAL]

Attest:

RUTH C. MASON
*Attesting Officer*

DONALD W. BANNER
*Commissioner of Patents and Trademarks*